(12) United States Patent
Folkenberg et al.

(10) Patent No.: US 9,777,253 B2
(45) Date of Patent: *Oct. 3, 2017

(54) LACTIC ACID BACTERIA FOR YOGHURT

(75) Inventors: Ditte Marie Folkenberg, Hillerød (DK); Christian Gilleladen, Copenhagen (DK); Helle Skov Guldager, Vedbæk (DK)

(73) Assignee: CHR. HANSEN A/S, Hoersholm (DK)

(*) Notice: Subject to any disclaimer, the term of this patent is extended or adjusted under 35 U.S.C. 154(b) by 194 days.

This patent is subject to a terminal disclaimer.

(21) Appl. No.: 13/805,988

(22) PCT Filed: Jun. 21, 2011

(86) PCT No.: PCT/EP2011/060302
§ 371 (c)(1),
(2), (4) Date: Mar. 7, 2013

(87) PCT Pub. No.: WO2011/161085
PCT Pub. Date: Dec. 29, 2011

(65) Prior Publication Data
US 2013/0164408 A1  Jun. 27, 2013

(30) Foreign Application Priority Data
Jun. 21, 2010  (EP) ..................... 10166614

(51) Int. Cl.
| | |
|---|---|
| A23C 9/127 | (2006.01) |
| C12N 1/20 | (2006.01) |
| A23C 9/123 | (2006.01) |
| C12N 15/01 | (2006.01) |
| C12R 1/225 | (2006.01) |
| C12R 1/46 | (2006.01) |

(52) U.S. Cl.
CPC ............. C12N 1/20 (2013.01); A23C 9/123 (2013.01); A23C 9/127 (2013.01); C12N 15/01 (2013.01); C12R 1/225 (2013.01); C12R 1/46 (2013.01)

(58) Field of Classification Search
CPC .......... A23C 9/123; A23C 9/127; C12N 1/20; C12N 15/01; C12R 1/225; C12R 1/46
USPC .......... 426/34, 42, 43, 580, 583; 435/252.9, 435/253.4
See application file for complete search history.

(56) References Cited

U.S. PATENT DOCUMENTS 8,865,238 B2   10/2014  Janzen et al.

FOREIGN PATENT DOCUMENTS

| | | |
|---|---|---|
| EP | 0 638 642 A1 | 2/1995 |
| JP | 2003-158997 | 6/2003 |
| WO | WO 03/096816 A1 | 11/2003 |
| WO | WO 2004/032655 A1 | 4/2004 |
| WO | WO-2007/095958 A1 | 8/2007 |
| WO | WO-2007/144770 A2 | 12/2007 |
| WO | WO-2007/147890 A1 | 12/2007 |
| WO | WO-2008/092458 A1 | 8/2008 |
| WO | WO-2011/092300 A1 | 8/2011 |
| WO | WO 2011/161085 A1 | 12/2011 |

OTHER PUBLICATIONS

Broadbent, J.R. et al., "Biochemistry, Genetics, and Applications of Exopolysaccharide Production in *Streptococcus thermophilus*: a Review[1]", Journal of Dairy Science, Feb. 1, 2003, vol. 86, No. 2, pp. 407-423.
Communication in EP Appln No. 10166614.7 dated Nov. 4, 2010.
Hassan, A. N. et al. "Microstructure and rheology of yogurt made with cultures differing only in their ability to produce exopolysaccharides", Journal of Dairy Science, May 1, 2003, vol. 86, No. 5, pp. 1632-1638.
Hess, S. J. et al. "Rheological Properties of Nonfat Yogurt Stabilized Using *Lactobacillus delbrueckii* ssp. Bulgaricus Producing Exopolysaccharide or Using Commercial Stabilizer Systems", Journal of Dairy Science, Feb. 1, 1997, vol. 80, No. 2, pp. 252-263.
International Search Report in PCT/EP2011/060302 dated Sep. 30, 2011.
Kang; "Effect of Single or Mixed Culture of Lactobacillus bulgaricus and *Streptococcus thermophiles* on Fermentation Characteristics of Buckwheat Sprout-added Yoghurt"; Korean J. Food Culture, 25(1):76-81 (Jan. 2010).

*Primary Examiner* — Leslie Wong
(74) *Attorney, Agent, or Firm* — Foley & Lardner LLP

(57) ABSTRACT

The present invention relates to a method for obtaining a lactic acid bacteria strain which results in a high mechanical shear resistance of the products fermented with the strain and to bacteria strains obtainable by such a method. Furthermore, the present invention relates to lactic acid bacteria strains which results in a high resistance towards mechanical shear treatment of the products fermented with the strains or mutants and variants thereof. The improved stability of the texture can be measured as reduced sedimentation in drinking yoghurt applications and reduced syneresis in set-type yoghurt applications. Thus, the present invention also relates to methods for preparation of a fermented milk product, such as a yoghurt, with such lactic acid bacteria strains and to such fermented milk products.

17 Claims, 2 Drawing Sheets

LACTIC ACID BACTERIA FOR YOGHURT

CROSS-REFERENCE TO RELATED APPLICATIONS

This application is a National Phase of International Application PCT/EP2011/060302, filed Jun. 21, 2011, which was published on Dec. 29, 2011 as WO 2011/161085 A1, which claims the benefit of EP Appln No. 10166614.7, filed Jun. 21, 2010, all of which are incorporated herein by reference in their entirety.

FIELD OF THE INVENTION

The present invention relates to a method for obtaining a lactic acid bacteria strain which results in a high mechanical shear resistance of the texture of the products fermented with the strain and to bacteria strains obtainable by such a method. The present invention also relates to use of such strains for preparing a fermented milk product and to the fermented milk product, such as a drinking yoghurt or a set-type yoghurt, with high mechanical shear resistance.

BACKGROUND ART

The food industry uses numerous bacteria, in particular lactic acid bacteria (LAB), in order to improve the taste and the texture of foods but also in order to extend the shelf life of these foods. In the case of the dairy industry, lactic acid bacteria are used intensively in order to bring about the acidification of milk (by fermentation) but also in order to texturize the product into which they are incorporated.

Among the lactic acid bacteria used in the food industry, there can be mentioned the genera *Streptococcus, Lactococcus, Lactobacillus, Leuconostoc, Pediococcus* and *Bifidobacterium*. Lactic acid bacteria of these genera are used extensively alone or in combination with other bacteria for the production of food products, in particular fermented products. They are used in particular in the formulation of the ferments used for the production of fermented milks, for example yoghurts. Certain of them play a dominant role in the development of the texture of the fermented product. This characteristic is closely linked to the production of polysaccharides.

Fermented milk drinks, such as e.g. drinking yoghurt, form a substantial and increasing market and often serves as background for functional ingredients as pre- and probiotics. There are significant differences between the texture challenges for the stirred yoghurt segment and the fermented milk drink segment. For fermented milk drinks, a high shear treatment after fermentation is often applied to break down the protein network in order to obtain smooth, homogeneous and drinkable products. However, this process has a dramatic cost on the mouth-feel of the fermented milk drink. This balance between smoothness and homogeneity on one side versus mouthfeel on the other side makes it difficult to obtain the optimal sensory profile. WO 2008/092458 relates to a drinking yoghurt with a casein:whey protein ratio of from 4:96 to 12:88 (w/w) which can be made without the formation of a coagulum after fermentation. By omitting coagulum formation the need of homogenization to break down the casein coagulum can thus be left out.

Lactic acid bacteria cultures currently on the market can typically not induce viscosity which is resistant to high shear treatment. As a consequence, thickeners like e.g. starch are often applied in fermented milk drinks to increase the mouthfeel.

Alternatively, an acceptable level of mouthfeel can be obtained by using full fat milk bases, but as the overall trend is a wish for low fat products with a 'clean label', i.e. no addition of stabilizing agents, there is a request for alternative solutions. As a consequence, there is a request for bacterial cultures for low fat fermented milk drinks replacing the effects of starch.

Such cultures must provide shear-resistant texture which can undergo shear treatment (up to e.g. 7 bar back pressure) and still maintain the required mouth-feel in combination with a smooth and homogeneous texture.

A lot of low fat and non-fat dairy products as for example set-type yoghurt have entered the market during the recent years. However, the reduction of the fat level has a great impact on the sensory and physical properties of the yoghurt. One factor that is highly affected is the texture properties. Due to weakening of the yoghurt gel caused by lower content of total solids the liquid phase will separate and form a layer on top of the yoghurt. This is referred to as syneresis and is regarded as a defect in the products. Different steps can be taken to reduce the syneresis as to increase the total solids by adding more protein and/or adding thickening agents as starch and gelatine. However these solutions are not very cost and label friendly. Therefore, a decrease in syneresis caused by the bacteria culture would be optimal and highly desirable.

Accordingly, there is a need for a method for obtaining additional lactic acid bacteria which result in an improved stability which can be measured as reduced sedimentation in drinking yoghurt and reduced syneresis in set-type yoghurt. Such lactic acid bacteria can be used in the production of fermented milk products, such as yoghurt, especially low fat or non-fat dairy products with reduced or no addition of thickeners, such as starch and pectin.

SUMMARY OF THE INVENTION

It is an object of the present invention to provide a method for obtaining lactic acid bacteria which result in a significantly increased mechanical shear resistance and improved stability of the products fermented with the strain.

It is another object of the present invention to provide such a lactic acid bacterium which result in a significantly increased mechanical shear resistance and improved stability capable of replacing the effects of thickeners, such as starch and pectin, while maintaining the required mouth-feel in combination with the desired smoothness and textural properties. Furthermore, it is an object of the present invention to provide methods for preparing fermented milk products with reduced sedimentation and syneresis and improved smoothness.

Additional objects will become apparent hereinafter and still others will be obvious to one skilled in the art to which the invention pertains.

The inventors have proceeded with extensive screening and research in order to achieve the above-described objects and solved the objects based on, in a first aspect, a method for obtaining a lactic acid bacteria strain that results in high resistance towards mechanical shear treatment, comprising:

a) heat treating skimmed milk base (0.1% fat, 12% protein) under suitable conditions, such as at 90° C. for 20 min.;

b) cooling the milk to between 40° C. to 43° C.;

c) inoculating the milk with between 0.01% to 0.03% F-DVS (between ~1×10$^6$ CFU/g to ~3×10$^6$ CFU/g) of said lactic acid bacteria;

d) fermenting said lactic acid bacteria strain at between 40° C. to 43° C. to pH 4.55;
e) post-treating the fermented milk obtained from step d) in a Post Treatment Unit comprising a plate heat exchanger and a back pressure valve wherein the plate heat exchanger is adapted to cool the yoghurt passing through the plate heat exchanger/back pressure valve system to 25° C. in less than 10 seconds and the back pressure valve is adjusted to provide a 7 bar back pressure, wherein the fermented milk is passed through the plate heat exchanger/back pressure valve system in less than 10 seconds such that the yoghurt is cooled to 25° C.;
f) measuring shear stress after post-treatment; and
g) selecting said lactic acid bacteria strain if the shear stress after 7 bar back pressure post-treatment is at least about 12 Pa.

A second aspect of the present invention relates to lactic acid bacteria strain obtainable by a method according to the first aspect of the invention, as well as biologically pure cultures and culture fractions containing the bacteria strain.

Specifically, the inventors have identified a *Lactobacillus bulgaricus* strain PIM-1966 and a *Streptococcus thermophilus* strain CHCC-11977 resulting in high resistance towards mechanical shear treatment and improved stability. The high shear resistance of the texture enables production of drinking yoghurts and results in an attractive high viscosity even after post treatment process. The improved stability can be measured as reduced sedimentation in drinking yoghurt application and reduced syneresis in set-type yoghurt application.

Another advantage of these strains is that it may be possible to use these as starting points to obtain mutated strains which result in even higher resistance towards mechanical shear treatment. Mutants and variants of *Lactobacillus bulgaricus* strain PIM-1966 and *Streptococcus thermophilus* CHCC-11977 which result in high resistance towards mechanical shear treatment are also part of the present invention.

Accordingly, a third aspect of the invention relates to a novel lactic acid bacteria strain selected from the group consisting of *Lactobacillus bulgaricus* strain PIM-1966 with accession No. DSM 23590 and *Streptococcus thermophilus* strain CHCC-11977 with accession No. DSM 22935, and mutants and variants of these strains, that results in high resistance towards mechanical shear treatment.

A fourth aspect of the invention relates to a method for preparing a fermented milk product comprising:
a) inoculating milk with a lactic acid bacteria strain according to the second or third aspect of the invention, or a mutant or variant thereof;
b) fermenting said milk with the lactic acid bacteria strain under favourable conditions;
c) optionally adding further microorganisms and/or additives to said milk;
d) optionally post-treating said milk; and
e) optionally packaging the fermented milk product.

In a fifth aspect the invention concerns a fermented milk product obtainable by the implementation of a method according to the fourth aspect of the invention.

In a sixth aspect the present invention relates to a fermented milk product comprising at least one lactic acid bacteria strain selected from the group consisting of *Lactobacillus bulgaricus* strain PIM-1966 with accession No. DSM 23590 and *Streptococcus thermophilus* strain CHCC-11977 with accession No. DSM 22935, and mutants and variants of these strains.

In a seventh aspect the present invention relates to a lactic acid ferment comprising a lactic acid bacterium according to the second or third aspect of the invention.

DETAILED DESCRIPTION OF THE INVENTION

Definitions

Figure 1:
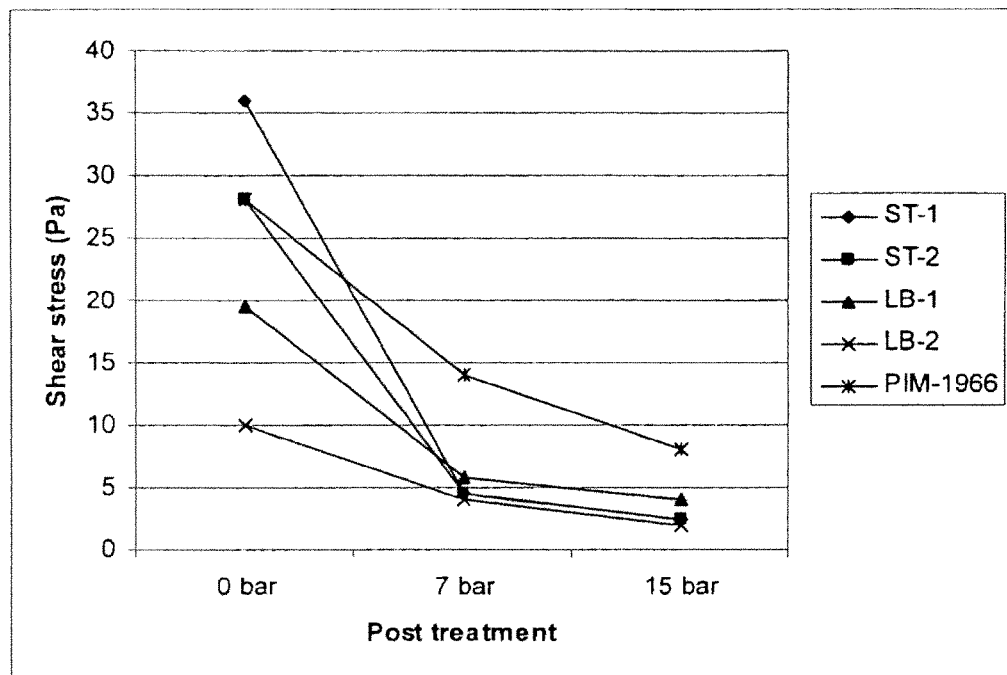
FIG. 1 depicts shear stress as a function of post treatment back pressure for 5 LAB strains.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as food cultures alone or in combination with other lactic acid bacteria. Lactic acid bacteria, including bacteria of the species *Lactobacillus* spp. and *Streptococcus thermophilus*, are normally supplied to the dairy industry either as frozen or freeze-dried cultures for bulk starter propagation or as so-called "Frozen Direct Vat Set" (F-DVS) cultures, intended for direct inoculation into a fermentation vessel or vat for the production of a dairy product, such as a fermented milk product. Such cultures are in general referred to as "starter cultures" or "starters".

The term "milk" is to be understood as the lacteal secretion obtained by milking any mammal, such as cows, sheep, goats, buffaloes or camels. In a preferred embodiment, the milk is cow's milk. The term milk also includes protein/fat solutions made of plant materials, e.g. soy milk.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid or liquid form (fermented milk product).

The term "stirred-type product" specifically refers to a fermented milk product which sustains a mechanical treatment after fermentation, resulting in a destructuration and liquefaction of the coagulum formed under the fermentation stage. The mechanical treatment is typically but not exclusively obtained by stirring, pumping, filtrating or homogenizing the gel, or by mixing it with other ingredients. Stirred-type products typically but not exclusively have a milk solid non-fat content of 9 to 15%.

The terms "set-type product" and "set-type yoghurt" include a product and a yoghurt, respectively, based on milk which has been inoculated with a starter culture and packaged next to the inoculating step and then fermented in the package.

The term "drinkable product" includes beverages such as "drinking yoghurt" and similar. The term "drinking yoghurt" typically covers a milk product produced by fermentation by the combination of *Lactobacillus* species and *Streptococcus thermophilus*. Drinking yoghurt typically has a milk solid non-fat content of 8% or more. Furthermore, the live culture count for drinking yoghurt drinks is typically at least $10^6$ cell forming units (CFU) pr ml.

"Mechanical post treatment" was carried out in a Post Treatment Unit featuring a plate heat exchanger and a back pressure valve. The yoghurt passes through the plate heat exchanger/back pressure valve system in <10 seconds. The Post Treatment Unit can operate at different temperatures (in this context 25° C. was applied) and different back pressures (in this context 0, 7 and 15 bar respectively were applied). Prior to this treatment the yoghurt coagulum was broken into liquid yoghurt by stirring.

"High shear treatment" in the present context refers to mechanical shear treatment with a back pressure above that which is suitable for stirred yoghurts, i.e. above about 3 bar.

In the present context, the term "shear stress" determines viscosity. Viscosity (unit is Pa s) is defined as Shear Stress (Pa)/Shear rate (1/s).

Shear stress value is reported as a standard herein at shear rate=300 1/s. Sensory experiments have shown (data not shown) that the best correlation between rheological measurements and sensory viscosity/mouth thickness are found when using the viscosity measured at shear rate 300 1/s.

The term "smoothness" herein refers to the lack of roughness of a texture and is determined by a smoothness sensory score given by a trained sensory panel as exemplified by Example 2. "Desirable smoothness" herein refers to a texture with a smoothness sensory score of above 7.

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same, or improved, properties (e.g. regarding viscosity, gel stiffness, mouth coating, flavor, post acidification, acidification speed, and/or phage robustness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant, less that 5%, or less than 1% or even less than 0.1% of the nucleotides in the bacterial genome have been shifted with another nucleotide, or deleted, compared to the mother strain.

In the present context, the term "variant" should be understood as a strain which is functionally equivalent to a strain of the invention, e.g. having substantially the same, or improved, properties (e.g. regarding viscosity, gel stiffness, mouth coating, flavour, and/or post acidification). Such variants, which may be identified using appropriate screening techniques, are a part of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Implementation and Aspects of the Invention

The inventors of the present invention have surprisingly identified that certain lactic acid bacteria result in a texture with high resistance towards mechanical post-treatment leading to the ability to produce a fermented milk product, such as a drinking yoghurt or a set-type yoghurt, with high viscosity, high level of mouth-feel, reduced sedimentation, reduced synersis and desirable smoothness without the need to add stabilizers, such as starch and pectin.

The inventors of the present invention have during the course of their work in a very perceptible manner developed a method for obtaining lactic acid bacteria which result in high resistance towards mechanical shear treatment. The method comprises a screening process in which the lactic acid bacteria are used to inoculate skimmed milk and left to ferment under standard fermentation conditions at between 40° C. to 43° C. to pH 4.55. After post-treating the resulting fermented milk with shear treatment at 7 bar back pressure and cooling to 25° C. the viscosity determined as shear stress is measured. Suitable lactic bacteria strains according to the present invention are selected if the shear stress of the fermented milk is at least at a threshold of about 12 Pa.

Accordingly, a first aspect of the present invention relates to a method for obtaining a lactic acid bacteria strain which results in high resistance towards mechanical shear treatment, comprising:
a) heat treating skimmed milk base (0.1% fat, 3.2% protein) under suitable conditions known to the skilled person, such as at 90° C. for 20 min.;
b) cooling the milk to between 40° C. to 43° C.;
c) inoculating the milk with between 0.01% to 0.02% F-DVS (between ~1×10$^6$ CFU/g to ~3×10$^6$ CFU/g) of said lactic acid bacteria;
d) fermenting the milk with said lactic acid bacteria strain at between 40° C. to 43° C. to pH 4.55;
e) post-treating the fermented milk obtained from step d) in a Post Treatment Unit comprising a plate heat exchanger and a back pressure valve wherein the plate heat exchanger is adapted to cool the yoghurt passing through the plate heat exchanger/back pressure valve system to 25° C. in less than 10 seconds and the back pressure valve is adjusted to provide a 7 bar back pressure, wherein the fermented milk is passed through the plate heat exchanger/back pressure valve system in less than 10 seconds such that the yoghurt is cooled to 25° C.;
f) measuring shear stress after post-treatment; and
g) selecting said lactic acid bacteria strain if the shear stress after 7 bar back pressure post-treatment is at least about 12 Pa.

In a preferred embodiment the shear stress after 7 bar back pressure post-treatment is at least about 13 Pa, such as at least about 14 Pa.

A second aspect of the invention relates to a lactic acid bacteria strain obtainable by the method according to the first aspect of the invention, as well as biologically pure cultures and fractions of cultures of the lactic bacteria strain.

A third aspect of the invention relates to the lactic acid bacteria strains selected from the group consisting of *Lactobacillus bulgaricus* strain PIM-1966 with accession No. DSM 23590 and *Streptococcus thermophilus* strain CHCC-11977 with accession No. DSM 22935, and mutants and variants of these strains resulting in the shear stress resistance characteristics of the deposited strains DSM 23590 or DSM 22935. respectively.

Preferably, the mutant or variant results in a shear stress resistance of at least about 5-40 Pa, more preferably 10-20 Pa. For example, the mutant of variant can have a shear stress resistance of about 12 Pa, 13 Pa, 14 Pa, 15 Pa, 16 Pa, 17 Pa, 18 Pa or 19 Pa.

LAB strains according to the present invention which result in high resistance towards mechanical shear treatment are particularly suitable for preparation of fermented milk products such as yoghurts. Particularly, in drinking yoghurt, stirred yoghurt, and set-type yoghurt applications such strains may reduce the need for addition of stabilizers, such as starch and pectin.

Accordingly, the present invention relates to a method for preparing a fermented milk product comprising inoculating milk with a lactic acid bacteria strain which result in a texture with high resistance towards mechanical shear treatment, and fermenting the milk under favorable conditions.

As is known to the skilled person various fermented milk products can be obtained by fermentation of milk with different lactic acid bacteria. In a preferred embodiment the fermented milk product is a product selected from the group consisting of yoghurt, drinking yoghurt, stirred yoghurt, set-type yoghurt and a yoghurt-like drink, bitter milk, butter milk, sour cream, fresh cheese and cheese.

In one preferred embodiment the fermented milk product is a drinking yoghurt. In another preferred embodiment the fermented milk product is a set-type yoghurt.

Generally speaking, the skilled person knows suitable fermenting conditions to ferment milk with the herein relevant bacteria, such as e.g. *Lactobacillus bulgaricus* and *Streptococcus thermophilus*. Herein suitable conditions include, but is not limited to, where the milk is inoculated with the bacteria and fermented at 38° C. to 43° C., until reaching a pH of 4.4 to 4.6 (roughly after around 8 hours). Cooling the milk to +6° C. stops the fermentation and growth.

The standard fermentation conditions may be modified if necessary by the person skilled in the art, on the basis of general knowledge and, possibly after routine experimentation. The culture medium is an appropriate medium for culturing the relevant strains.

In a preferred embodiment the lactic acid bacteria strain used for inoculating the milk is selected from the group comprising *Lactobacillus bulgaricus* strain PIM-1966 with accession No. DSM 23590 and *Streptococcus thermophilus* strain CHCC-11977 with accession No. DSM 22935, and mutants and variants of these strains.

The *Lactobacillus bulgaricus* strain PIM-1966, and mutants and variants thereof, and the *Streptococcus thermophilus* strain CHCC-11977, and mutants and variants thereof, are inoculated with from 1×10$^4$ to 1×10$^7$ CFU (colony forming units) of bacteria per ml of milk substrate.

Measuring the viable cell count is done by quantifying the number of colony forming units (CFU) of bacteria in serial dilutions by colony counting on agar plates, according to standard methods in the art. Suitable medium and incubation conditions are known to the skilled person and as given in the Examples below.

If desired, one may add extra bacteria (e.g. extra *Lactobacillus bulgaricus* strain PIM-1966) at some point of interest (e.g. after completion of the fermentation).

The milk may in step a) be inoculated with at least one other strain of lactic acid bacteria. It should be understood that the milk may be inoculated separately/sequentially with each bacterial species, or simultaneously with two or more bacterial species. It is presently preferred that the milk is inoculated with all bacterial species at the same time. This is conveniently done by inoculating the milk with a starter culture comprising the bacterial species.

According to a preferred embodiment the at least one strain of bacteria is one or more bacteria of the genus *Lactococcus, Streptococcus, Lactobacillus, Leuconostoc, Pseudoleuconostoc, Pediococcus, Brevibacterium, Enterococcus, Propionibacterium* and *Bifidobacterium*.

In a specially preferred embodiment of the present invention, said at least one other strain of lactic acid bacteria comprises at least one strain of *Streptococcus thermophilus* and/or at least one strain of *Lactobacillus bulgaricus*.

In the present context the at least one strain of *Streptococcus thermophilus* may be any suitable (e.g. commercially available) *Streptococcus thermophilus* strain. As known to the skilled person, the strains may be inoculated in adequate amounts to obtain an adequate amount of *Streptococcus thermophilus* in the final fermented milk product.

In the present context the at least one strain of *Lactobacillus bulgaricus* may be any suitable (e.g. commercially available) *Lactobacillus bulgaricus* strain. As known to the skilled person, the strains may be inoculated in adequate amounts to obtain an adequate amount of *Lactobacillus bulgaricus* in the final fermented milk product.

In a preferred embodiment the milk is inoculated with from $10^4$ to $10^7$ CFU of the at least one strain of *Streptococcus thermophilus* per ml of milk substrate and/or with from $10^4$ to $10^7$ CFU of the at least one strain of *Lactobacillus bulgaricus* per ml of milk substrate.

According to a preferred embodiment of the present invention the milk is post-treated by high shear treatment in a Post Treatment Unit featuring a plate heat exchanger adjusted to cool to 25° C. and a back pressure valve adjusted to provide a suitable back pressure. The yoghurt passes through the plate heat exchanger/back pressure valve system in <10 seconds.

In a preferred embodiment the high shear treatment is treatment with 3 to 15 bar back pressure. In an even more preferred embodiment the high shear treatment is treatment with 6 to 8 bar back pressure. Preferably, the high shear treatment is treatment with about 7 bar back pressure.

According to another embodiment the milk is not post-treated but left to settle after fermentation.

In a particular preferred embodiment no stabilizers are added to the milk.

According to an embodiment of the present invention, the fermented milk product is conveniently packaged in a sealed package that contains from 10-5000 ml of the product, such as from 25 to 3000 ml or from 50 to 1000 ml. Exemplary packages may contain 10-300 ml, 20-200 ml or 30-100 ml.

A further aspect of the present invention is a fermented milk product obtainable by the method of preparing a fermented milk product.

Another aspect of the present invention is a fermented milk product comprising at least one lactic acid bacteria strain according to the second or third aspect of the invention.

In a preferred embodiment such fermented milk product is a yoghurt. Preferably, a drinking yoghurt or a set-type yoghurt.

Fermented milk products as described herein can also be used as an additive to e.g. be put into other edible food products, such as curd cheeses, chocolates, juices, meat products and dried milk powder products for young infants (infant formulas).

Another aspect relates to a lactic ferment comprising at least one lactic acid bacteria strain according to the second or third aspect of the present invention, or a mutant or a variant thereof.

In a preferred embodiment the lactic ferment comprises *Lactobacillus bulgaricus* strain PIM-1966 or a mutant or a variant thereof. In another preferred embodiment the lactic ferment comprises *Streptococcus thermophilus* strain CHCC-11977 or a mutant or a variant thereof.

In a preferred embodiment of the present invention the lactic ferment is in frozen, freeze-dried or liquid form.

Embodiments of the present invention are described below, by way of non-limiting examples.

EXAMPLES

Example 1

Development of Phage Resistant Mutants from *Lb. delbrueckii* subsp. *bulgaricus* LB-1 with Improved Texture Properties.

From the mother strain LB-1, phage resistant mutants were isolated as follows. Mutants were picked from MRS agar plates containing 10 mM $CaCl_2$/10 mM $MgCl_2$ after plating 0.1 ml of an over night culture of LB-1 together with 0.1 ml of a CHPC658 phage lysate containing $10^6$ phage particles per ml and anaerobic incubation for two days at 37° C.

Thirty mutants were isolated and tested in cross-streaking towards phage strain CHPC658. Twenty-nine mutants appeared resistant in the cross-streaking test, and were afterwards three times colony-purified on MRS agar plates.

The 29 mutants were tested in microtiter plates for acidification profile and phage resistance. Two microtiter plates were prepared with milk and each plate was inoculated with 2% of the respective mutant. For one plate, 2% peptone-salt diluent (control) was added to each well, and to the other microtiter plate 2% CHPC658 phage strain containing $10^6$ phage particles per ml was added. The two plates were incubated at 37° C. for two days, and pH of each well was recorded every 12 minutes. The majority of the phage resistant mutants revealed an acidification profile which was comparable to the mother strain (pH ca. 5.5 after 24 hours). All mutants were phage resistant compared to the mother strain LB-1, which was attacked by phage strain CHPC658.

The mutant, LB-4 was chosen to be tested for shear treatment resistance based on the acidification profile (similar to the mother strain) and the viscosity parameters of the strain.

Example 2

The shear resistance towards mechanical post treatment of the texture of the fermented milk made with several lactic acid bacteria strains was investigated in a drinking yoghurt application using 3 different levels of post treatment (0, 7 and 15 bar back pressure). ST-1 and ST-2 are *Streptococcus thermophilus* strains whereas LB-1, LB-2 and PIM-1966 are *Lactobacillus bulgaricus* strains.

Experimental

The study was performed in two replicates and the average values are given. All strains were fermented together with helper strains in order to obtain comparable fermentation times for all samples (see TABLE 1).

Production

4 L of yoghurt of each culture was produced using a skimmed milk base (0.1% fat, 3.2% protein, 8% sucrose). The milk was heat-treated for 20 min at 90° C. and cooled to fermentation temperature 43° C. Hereafter the milk was inoculated with a total of 0.02% F-DVS culture according to TABLE 1. Helper strains were used in order to achieve similar fermentation times. CHCC-7018 is a proteolytic *Streptococcus thermophilus* strain with no exopolysaccharide (EPS) production i.e. contributing to a 'fast' acidification but not to texture. CHCC-4351 is a *Lactobacillus bulgaricus* strain with no EPS production i.e. contributing to acidification but not to texture. The milk was fermented to pH 4.55. The yoghurts were then post processed and cooled to 25° C. in a Post Treatment Unit (PTU). For each yoghurt, samples were taken out after post treatment with a back pressure of respectively 0 bar, 7 bar and 15 bar.

TABLE 1

Cultures, fermentation temperature and post treatments applied

| Species | Test strain conc. | Helper: St-7018 | Helper: Lb-4351 | Fermentation temperature | Post treatments: |
|---|---|---|---|---|---|
| Streptococcus thermophilus | 90% | 5% | 5% | 43 | 0; 7; 15 bar |
| Lactobacillus bulgaricus | 90% | 10% | | 43 | 0; 7; 15 bar |

Analyses

The yoghurts were characterized with respect to:

Rheology: on an Anton Paar MCR Rheometer fitted with and Automatic sample Changer (Anton Paar, Austia) using a drinking yoghurt set-up with a BOB/COP measuring system. Flow curves measuring the shear stress as a function of shear rates (0 1/s-300 1/s-0 1/s) were collected.

Sensory properties: samples post treated with 7 bar back pressure were evaluated in the lab by an 'expert panel'. A smoothness score (scale 0-9) was given.

Stability towards sedimentation: was studied using Turbiscan.

Results

TABLE 2 shows the results from Rep I and II, respectively.

TABLE 2

Fermentation time, shear stress and smoothness scores in average over 2 repetitions.

| | Post treatment (bar) | Time to pH 4.55 (min) | Shear stress (Pa) | Smoothness sensory score (0-9 scale) |
|---|---|---|---|---|
| ST-1 | 0 | 365 | 36.0 | not evaluated |
| ST-1 | 7 | 365 | 4.5 | 4 |
| ST-1 | 15 | 365 | 2.5 | not evaluated |
| ST-2 | 0 | 375 | 28 | not evaluated |
| ST-2 | 7 | 375 | 4.5 | 2 |
| ST-2 | 15 | 375 | 2.5 | not evaluated |
| LB-1 | 0 | 370 | 19.5 | not evaluated |
| LB-1 | 7 | 370 | 6.0 | 8 |
| LB-1 | 15 | 370 | 4.0 | not evaluated |
| PIM-1966 | 0 | 360 | 28.0 | not evaluated |
| PIM-1966 | 7 | 360 | 14.0 | 9 |
| PIM-1966 | 15 | 360 | 8.0 | not evaluated |
| LB-2 | 0 | 410 | 10.0 | not evaluated |
| LB-2 | 7 | 410 | 4.0 | 4 |
| LB-2 | 15 | 410 | 2.0 | not evaluated |

FIG. 1 shows the shear stress as a function of post treatment back pressure in replicate over two trials.

Figure 2:
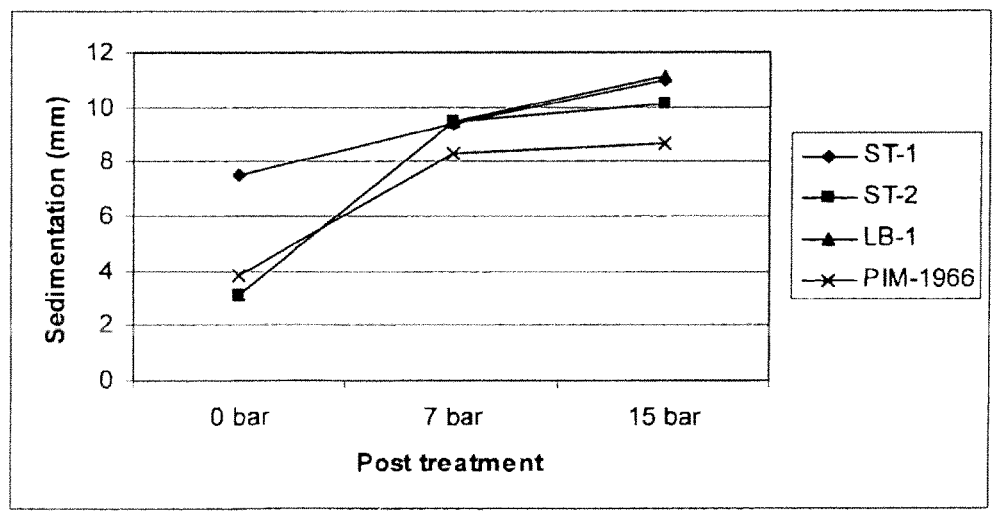
FIG. 2 shows sedimentation as a function of post treatment for drinking yoghurt made with 4 different LAB strains. Sedimentation measured after 21 days of storage.

FIG. 2 shows sedimentation as a function of post treatment for drinking yoghurt made with 4 different strains. Sedimentation measured after 21 days of storage.

Discussion

Shear Resistance:

As apparent from Table 2 and FIG. 1 there is a large variety of initial texture levels (0 bar post treatment) from 10-36 Pa. However, after a post treatment of 7 bar back pressure, the span is down to 4-14 Pa. After 15 bar post treatment the range spanned is 2-8 Pa. It is evident, that the strain PIM-1966 results in texture which is remarkably resistant to mechanical post treatment compared to the texture resulting from other strains. Although the presence of PIM-1966 does not result in a particularly high shear stress prior to post treatment (the 0 bar sample) the texture is significantly more viscous than that of any other strain after respectively 7 bar and 15 bar post treatment.

Stability:

Generally a higher post treatment results in a lower stability (more sedimentation).

The best stability is found in drinking yoghurt produced with PIM-1966 which has the lowest level of sedimentation after 21 days storage—this applies both for 7 bar and post treatment.

Sensory Evaluation:

Drinking yoghurt made with PIM-1966 was evaluated to have very high smoothness by a sensory expert group (score 9 out of 9).

Conclusion

In conclusion the strain PIM-1966 is unique due to the resulting high resistance towards mechanical shear stress, it also provides high smoothness and stability towards sedimentation in drinking yoghurt application compared to LAB strains which provide a shear stress of below 12 Pa after 7 bar back pressure post treatment.

Example 3

In order to identify other LAB strains which result in high resistance towards mechanical shear stress, several strains were screened according to the present invention for shear stress above about 12 Pa after post treatment with 7 bar back pressure in drinking yoghurt application. PIM-1966 was included again as a positive control.

Experimental

The study was performed in two replicates. All strains were fermented together with helper strains in order to obtain comparable fermentation times for all samples (see TABLE 1). ST-1, ST-2, ST-4, ST-5, ST-6, ST-7 and CHCC-11977 are Streptococcus thermophilus strains whereas LB-1, LB-4, LB-5 and PIM-1966 are Lactobacillus bulgaricus strains.

Production

Production was carried out as in Example 1.

Analyses

The yoghurts were characterized with respect to rheology:

For the trials we measured shear stress as a function of shear rates spanning from 0 to 300 1/s—this provides so called flow curves.

The equipment is an Anton Paar MCR Rheometer fitted with an Automatic sample Changer (Anton Paar, Austia) using a drinking yoghurt set-up with a BOB/COP measuring system. Flow curves measuring the shear stress as a function of shear rates (0 1/s-300 1/s-0 1/s) were collected.

TABLE 3

Shear stress as function of post treatment back pressure in average over 2 repititions.

| Back pressure | 0 bar | 7 bar | 15 bar |
|---|---|---|---|
| ST-1 | 36 | 4.5 | 2.5 |
| ST-2 | 28 | 4.5 | 2.5 |
| CHCC-11977 | 41.6 | 13.1 | 4.9 |
| ST-4 | 37.5 | 10 | 4 |
| ST-5 | 36.5 | 7.5 | 3 |
| ST-6 | 35 | 11.5 | 4.2 |
| ST-7 | 29 | 7.8 | 3.9 |
| LB-1 | 19 | 8.4 | 6 |
| PIM-1966 | 35 | 18.5 | 14.6 |
| LB-3 | 34 | 22 | 16.6 |

TABLE 3-continued

Shear stress as function of post treatment back pressure in average over 2 repititions.

| Back pressure | 0 bar | 7 bar | 15 bar |
|---|---|---|---|
| LB-4 | 23 | 12 | 9.9 |
| LB-5 | 14 | 4.6 | 3.4 |

Results

Figure 3:
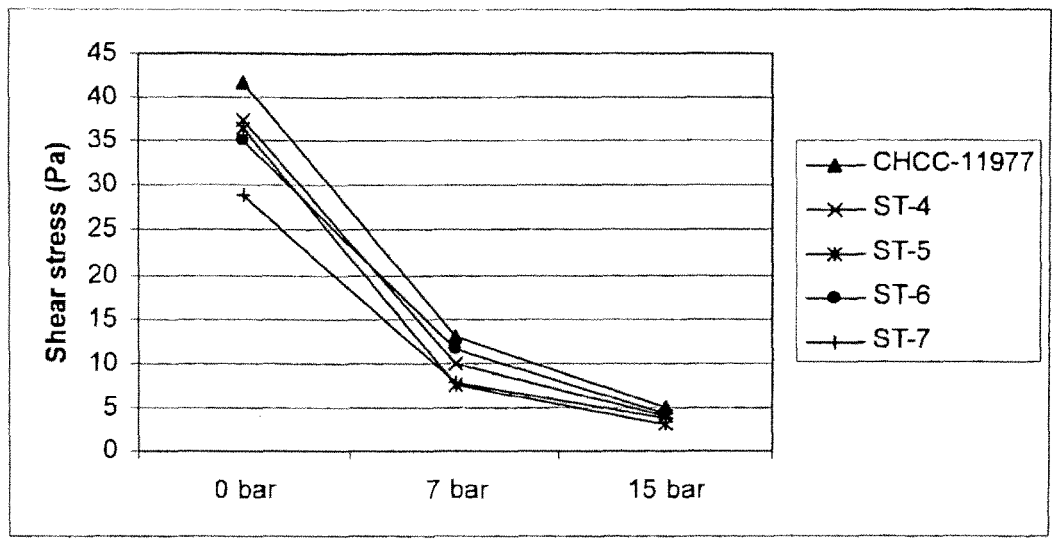
FIG. 3 depicts shear stress as a function of post treatment back pressure for 5 *Streptococcus thermophilus* strains.
Figure 4:
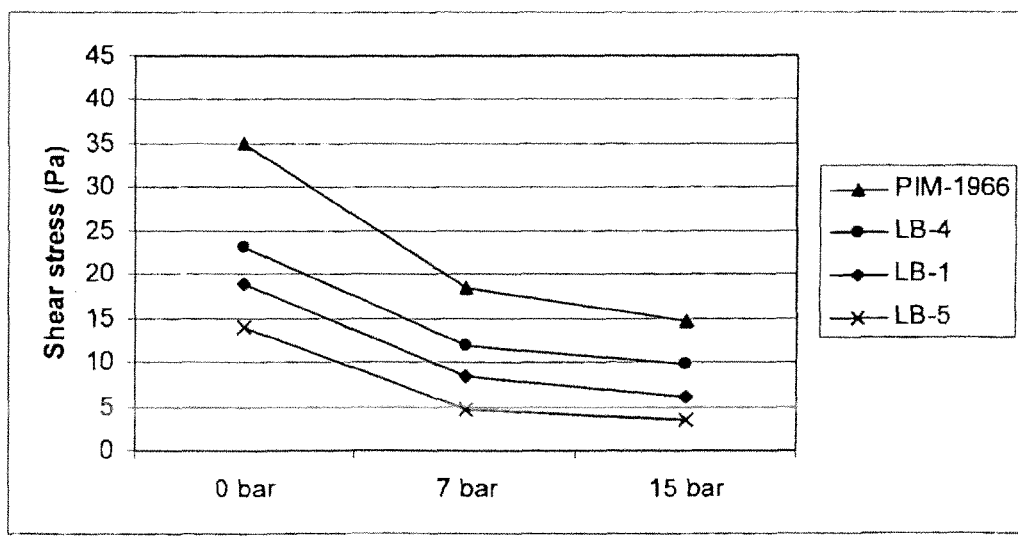
FIG. 4 depicts shear stress as a function of post treatment back pressure for 5 *Lactobacillus bulgaricus* strains.

FIGS. 3 and 4 show the shear stress as a function of post treatment back pressure in replicate over two trials. FIG. 3 depicts the *Streptococcus thermophilus* strains and FIG. 4 depicts the *Lactobacillus bulgaricus* strains.

Conclusion

The mutant to PIM-1966, LB-3 was found to result in an even higher resistance towards mechanical shear treatment and higher viscosity than PIM-1966. Additionally, a *Streptococcus thermophilus* strain, CMC[-11977, was found to also result in high mechanical shear resistance according to the present invention. ST-11977 provides high viscosity and high smoothness in drinking yoghurt application.

Deposits and Expert Solution

The applicant requests that a sample of the deposited microorganisms stated below may only be made available to an expert, until the date on which the patent is granted.

The *Lactobacillus bulgaricus* strain PIM-1966 was deposited 2010 May 6 at Deutsche Sammlung von Mikroorganismen und Zellkulturen GmbH, Inhoffenstr. 7B, D-38124 Braunschweig (DSMZ) and given the accession No.: DSM 23590

The *Streptococcus thermophilus* strain CHCC11977 was deposited 2009 Sep. 8 at Deutsche Sammlung von Mikroorganismen und Zellkulturen GmbH, Inhoffenstr. 7B, D-38124 Braunschweig (DSMZ) and given the accession No.: DSM 22935.

The deposits were made according to the Budapest treaty on the international recognition of the deposit of microorganisms for the purposes of patent procedure.

REFERENCES

WO 2008/092458

The invention claimed is:

1. A method for obtaining a selected lactic acid bacteria strain that induces mechanical shear resistance in a fermented milk product as measured as the shear stress after subjecting the fermented milk to a back pressure of 7 bar, comprising:
   a) heat treating a skimmed milk comprising 0.1% fat and 3.2% protein;
   b) cooling the milk to between 40° C. to 43° C.;
   c) inoculating the milk with between 0.01% to 0.03% F-DVS (between ~1×10$^6$ CFU/g to ~3 ×10$^6$ CFU/g) of a lactic acid bacteria strain;
   d) fermenting the milk with said lactic acid bacteria strain at between 40° C. to 43° C. to pH 4.55;
   e) post-treating the fermented milk obtained from step d) in a Post Treatment Unit comprising a plate heat exchanger and a back pressure valve wherein the plate heat exchanger is adapted to cool the fermented milk passing through the plate heat exchanger/back pressure valve system to 25° C. in less than 10 seconds and the back pressure valve is adjusted to provide a 7 bar back pressure, wherein the fermented milk is passed through the plate heat exchanger/back pressure valve system in less than 10 seconds such that the fermented milk is cooled to 25° C.;
   f) measuring shear stress after said post-treatment; and
   g) selecting said lactic acid bacteria strain if the shear stress after 7 bar back pressure post-treatment is at least about 12 Pa.

2. A method for preparing a fermented milk product comprising:
   a) inoculating milk with a lactic acid bacteria strain selected from strains that induce mechanical shear resistance in a fermented milk;
   b) fermenting said milk with the lactic acid bacteria strain;
   c) optionally adding further microorganisms and/or additives to said milk;
   d) optionally post-treating said milk; and
   e) optionally packaging the fermented milk product,
   wherein the lactic acid bacteria strain is selected from the group consisting of:
      (i) the *Lactobacillus bulgaricus* strain PIM1966 that was deposited with the Deutsche Sammlung von Mikroorganismen und Zellkulturen under Accession No. DSM 23590 and strains derived therefrom exhibiting the same or improved induction of mechanical shear resistance in a fermented milk as the deposited strain PIM1966; and
      (ii) the *Streptococcus thermophilus* strain CHCC11977 that was deposited with the Deutsche Sammlung von Mikroorganismen und Zellkulturen under Accession No. DSM 22935 and strains derived therefrom exhibiting the same or improved induction of mechanical shear resistance in a fermented milk product as the deposited strain CHCC11977,
   wherein the ability of a lactic acid bacteria strain to induce mechanical shear resistance in a fermented milk is assessed by subjecting a milk fermented with the strain to a back pressure of 7 bar and thereafter measuring shear stress of the fermented milk.

3. The method according to claim 2, wherein step (a) further comprises inoculating the milk with at least one other strain of lactic acid bacteria.

4. The method according to claim 3, wherein the at least one other strain of lactic acid bacteria comprises at least one strain of *Streptococcus thermophilus* and/or at least one strain of *Lactobacillus bulgaricus*.

5. The method according to claim 2, wherein step (a) comprises inoculating the milk with (i) the *Streptococcus thermophilus* strain CHCC11977 that was deposited with the Deutsche Sammlung von Mikroorganismen und Zellkulturen under Accession No. DSM 22935, or the strain derived therefrom having the same or improved induction of mechanical shear resistance in fermented milk product as the strain CHCC11977 deposited under Accession No. DSM 22935, and (ii) the *Lactobacillus bulgaricus* strain PIM1966 that was deposited with the Deutsche Sammlung von Mikroorganismen und Zellkulturen under Accession No. DSM 23590, or the strain derived therefrom having the same or improved induction of mechanical shear resistance in a fermented milk product as the strain PIM1966 deposited under Accession No. DSM 23590.

6. The method according to claim 2, wherein the method comprises post-treating said milk by high shear treatment.

7. The method according to claim 6, wherein said high shear post-treatment is with 3 to 15 bar back pressure.

8. The method according to claim 2, wherein said milk is not post-treated but is left to settle after fermentation.

9. The method according to claim 2, wherein no stabilizing agents are added to the milk.

10. A dairy product comprising:
(a) a fermented milk product, and
(b) at least one lactic acid bacteria strain that induces mechanical shear resistance in a fermented milk product, selected from the group consisting of:
(i) the *Lactobacillus bulgaricus* strain PIM1966 that was deposited with the Deutsche Sammlung von Mikroorganismen und Zellkulturen under Accession No. DSM 23590 and strains derived therefrom exhibiting the same or improved induction of mechanical shear resistance in a fermented milk product as the deposited strain PIM1966 deposited under Accession No. DSM 23590, and
(ii) the *Streptococcus thermophilus* strain CHCC11977 that was deposited with the Deutsche Sammlung von Mikroorganismen and Zellkulturen under Accession No. DSM 22935 and strains derived therefrom exhibiting the same or improved induction of mechanical shear resistance in a fermented milk product as the strain CHCC11977 deposited under Accession No. DSM 22935,
wherein the ability of a lactic acid bacteria strain to induce mechanical shear resistance in a fermented milk is assessed by subjecting a milk fermented with the strain to a back pressure of 7bar and thereafter measuring shear stress of the fermented milk.

11. The dairy product according to claim 10, wherein the fermented milk product is a yoghurt.

12. The dairy product according to claim 11, wherein the yoghurt is a drinking yoghurt.

13. The dairy product according to claim 11, wherein the yoghurt is a set-type yoghurt.

14. A fermented milk product made by the method of claim 2.

15. The fermented milk product according to claim 14, wherein the fermented milk product is a yoghurt.

16. The fermented milk product according to claim 15, wherein the yoghurt is a drinking yoghurt.

17. The fermented milk product according to claim 15, wherein the yoghurt is a set-type yoghurt.

* * * * *